United States Patent
Trautwein et al.

(10) Patent No.: US 11,160,585 B2
(45) Date of Patent: Nov. 2, 2021

(54) INSTRUMENT SYSTEM FOR USE WITH AN INTERSPINOUS IMPLANT

(71) Applicant: Paradigm Spine, LLC, New York, NY (US)

(72) Inventors: Frank T. Trautwein, Filderstadt (DE); Ralf Riesinger, Wurmlingen (DE)

(73) Assignee: PARADIGM SPINE, LLC, New York, NY (US)

( * ) Notice: Subject to any disclaimer, the term of this patent is extended or adjusted under 35 U.S.C. 154(b) by 229 days.

(21) Appl. No.: 16/126,381

(22) Filed: Sep. 10, 2018

(65) Prior Publication Data

US 2019/0083145 A1 Mar. 21, 2019

Related U.S. Application Data

(62) Division of application No. 14/486,625, filed on Sep. 15, 2014, now Pat. No. 10,070,898, which is a division of application No. 11/790,727, filed on Apr. 27, 2007, now Pat. No. 8,834,482.

(60) Provisional application No. 60/796,256, filed on Apr. 28, 2006.

(51) Int. Cl.
 *A61B 17/70* (2006.01)
 *A61B 17/88* (2006.01)
 *A61B 17/56* (2006.01)

(52) U.S. Cl.
 CPC ...... *A61B 17/7065* (2013.01); *A61B 17/7062* (2013.01); *A61B 17/7067* (2013.01); *A61B 17/8863* (2013.01); *A61B 2017/564* (2013.01)

(58) Field of Classification Search
 CPC ............ A61B 17/7062; A61B 17/7065; A61B 17/7067; A61B 17/7068; A61B 2017/564
 See application file for complete search history.

(56) References Cited

U.S. PATENT DOCUMENTS

| | | | |
|---|---|---|---|
| 5,011,484 A | 4/1991 | Breard |
| 5,496,318 A | 3/1996 | Howland et al. |
| 5,645,599 A | 7/1997 | Samani |
| 5,836,948 A | 11/1998 | Zucherman et al. |
| 5,860,977 A | 1/1999 | Zucherman et al. |
| 5,876,404 A | 3/1999 | Zucherman et al. |

(Continued)

FOREIGN PATENT DOCUMENTS

| | | |
|---|---|---|
| CN | 1849105 A | 10/2006 |
| EP | 0322334 A1 | 6/1989 |

(Continued)

*Primary Examiner* — Anu Ramana
(74) *Attorney, Agent, or Firm* — Farber LLC

(57) ABSTRACT

A surgical instrument system comprises surgical instruments for use with an implantable interspinous device having at least one pair of wings for securing the implantable device to a spinous process. The instrument system may include a surgical instrument for expanding or spreading the pair of wings to accommodate the spinous process. Further, a surgical instrument may be provided for crimping or compressing the pair of wings against the spinous process for secure attachment of the device to a vertebra. The surgical instruments may be configured similar to pliers and apply force to the pair of wings within a predetermined range so as to avoid damage, weakening or breakage of the pair of wings. The surgical instrument system may also include interspinous devices of differing sizes.

19 Claims, 9 Drawing Sheets

(56) References Cited

U.S. PATENT DOCUMENTS

| | | |
|---|---|---|
| 5,951,553 A | 9/1999 | Betz et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,238,397 B1 | 5/2001 | Zucherman et al. |
| 6,280,444 B1 | 8/2001 | Zucherman et al. |
| 6,332,882 B1 | 12/2001 | Zucherman et al. |
| 6,332,883 B1 | 12/2001 | Zucherman et al. |
| 6,379,355 B1 | 4/2002 | Zucherman et al. |
| 6,402,750 B1 | 6/2002 | Atkinson et al. |
| 6,419,676 B1 | 7/2002 | Zucherman et al. |
| 6,419,677 B2 | 7/2002 | Zucherman et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,582,433 B2 | 6/2003 | Yun |
| 6,626,944 B1 | 9/2003 | Taylor |
| 6,652,527 B2 | 11/2003 | Zucherman et al. |
| 6,652,534 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,733,534 B2 | 5/2004 | Sherman |
| 6,761,720 B1 | 7/2004 | Senegas |
| 6,796,983 B1 | 9/2004 | Zucherman et al. |
| 6,902,566 B2 | 6/2005 | Zucherman et al. |
| 7,090,679 B2 | 8/2006 | Saint-Martin et al. |
| 7,252,673 B2 | 8/2007 | Lim |
| 7,871,426 B2 | 1/2011 | Chin et al. |
| 7,922,750 B2 | 4/2011 | Trautwein et al. |
| 7,985,246 B2 | 7/2011 | Trieu |
| 7,988,698 B2 | 8/2011 | Rosenberg et al. |
| 8,419,738 B2 | 4/2013 | Smisson et al. |
| 8,430,911 B2 | 4/2013 | Chin et al. |
| 8,439,951 B2 | 5/2013 | Trautwein et al. |
| 8,500,778 B2 | 8/2013 | Jackson et al. |
| 2002/0072752 A1 | 6/2002 | Zucherman et al. |
| 2002/0111679 A1* | 8/2002 | Zucherman ............ A61K 31/37 623/17.11 |
| 2003/0216736 A1 | 11/2003 | Robinson et al. |
| 2004/0143332 A1 | 7/2004 | Krueger et al. |
| 2004/0147936 A1 | 7/2004 | Rosenberg et al. |
| 2004/0153071 A1* | 8/2004 | Zucherman ........ A61B 17/7068 606/249 |
| 2004/0153072 A1 | 8/2004 | Bonutti |
| 2004/0162617 A1 | 8/2004 | Zucherman et al. |
| 2004/0181282 A1 | 9/2004 | Zucherman et al. |
| 2004/0199255 A1 | 10/2004 | Mathieu et al. |
| 2004/0220568 A1 | 11/2004 | Zucherman et al. |
| 2004/0243239 A1 | 12/2004 | Taylor |
| 2005/0010293 A1 | 1/2005 | Zucherman et al. |
| 2005/0010298 A1 | 1/2005 | Zucherman et al. |
| 2005/0015095 A1 | 1/2005 | Keller |
| 2005/0038511 A1* | 2/2005 | Martz ................ A61B 17/1671 623/17.11 |
| 2005/0055031 A1 | 3/2005 | Lim |
| 2005/0075634 A1 | 4/2005 | Zucherman et al. |
| 2005/0101955 A1 | 5/2005 | Zucherman et al. |
| 2005/0102028 A1 | 5/2005 | Arnin et al. |
| 2005/0143738 A1 | 6/2005 | Zucherman et al. |
| 2005/0165398 A1 | 7/2005 | Reiley et al. |
| 2005/0196240 A1 | 9/2005 | Zucherman et al. |
| 2005/0203512 A1 | 9/2005 | Hawkins et al. |
| 2005/0203624 A1 | 9/2005 | Serhan et al. |
| 2005/0209603 A1 | 9/2005 | Zucherman et al. |
| 2005/0216017 A1 | 9/2005 | Fielding et al. |
| 2005/0228383 A1 | 10/2005 | Zucherman et al. |
| 2005/0228384 A1 | 10/2005 | Zucherman et al. |
| 2005/0261768 A1 | 11/2005 | Trieu |
| 2006/0030860 A1 | 2/2006 | Peterman |
| 2006/0293662 A1* | 12/2006 | Boyer, II ........... A61B 17/7065 606/249 |
| 2007/0162040 A1 | 7/2007 | Grabowski et al. |
| 2007/0233076 A1 | 10/2007 | Trieu |
| 2008/0208344 A1 | 8/2008 | Kilpela et al. |
| 2008/0228225 A1 | 9/2008 | Trautwein et al. |
| 2009/0062869 A1 | 3/2009 | Claverie et al. |
| 2010/0087860 A1 | 4/2010 | Chin et al. |
| 2011/0022090 A1 | 1/2011 | Gordon et al. |
| 2011/0190819 A1 | 8/2011 | Trautwein et al. |
| 2011/0224740 A1 | 9/2011 | Smisson et al. |
| 2012/0078302 A1 | 3/2012 | Reimels |
| 2013/0041408 A1 | 2/2013 | Dinville et al. |
| 2014/0005723 A1 | 1/2014 | Shah et al. |

FOREIGN PATENT DOCUMENTS

| | | |
|---|---|---|
| EP | 1138268 A1 | 10/2001 |
| EP | 1330987 A1 | 7/2003 |
| FR | 2703239 A1 | 10/1994 |
| FR | 2717675 A1 | 9/1995 |
| WO | 94/26192 A1 | 11/1994 |
| WO | 99/40866 A1 | 9/1999 |
| WO | 2004/024010 A1 | 3/2004 |
| WO | 2004/073533 A1 | 9/2004 |
| WO | 2004/084743 A1 | 10/2004 |
| WO | 2005/009300 A1 | 2/2005 |
| WO | 2005/020860 A2 | 3/2005 |
| WO | 2005/110258 A1 | 11/2005 |

\* cited by examiner

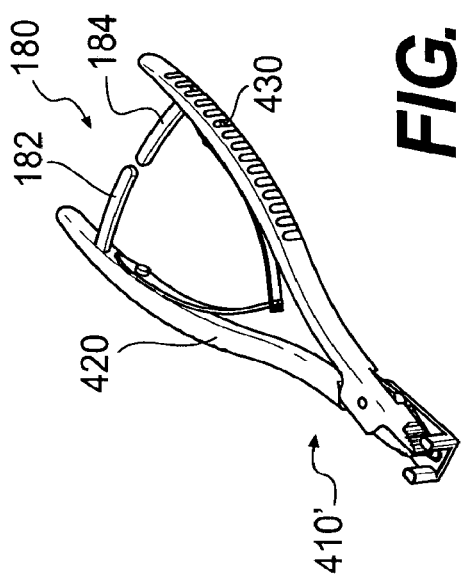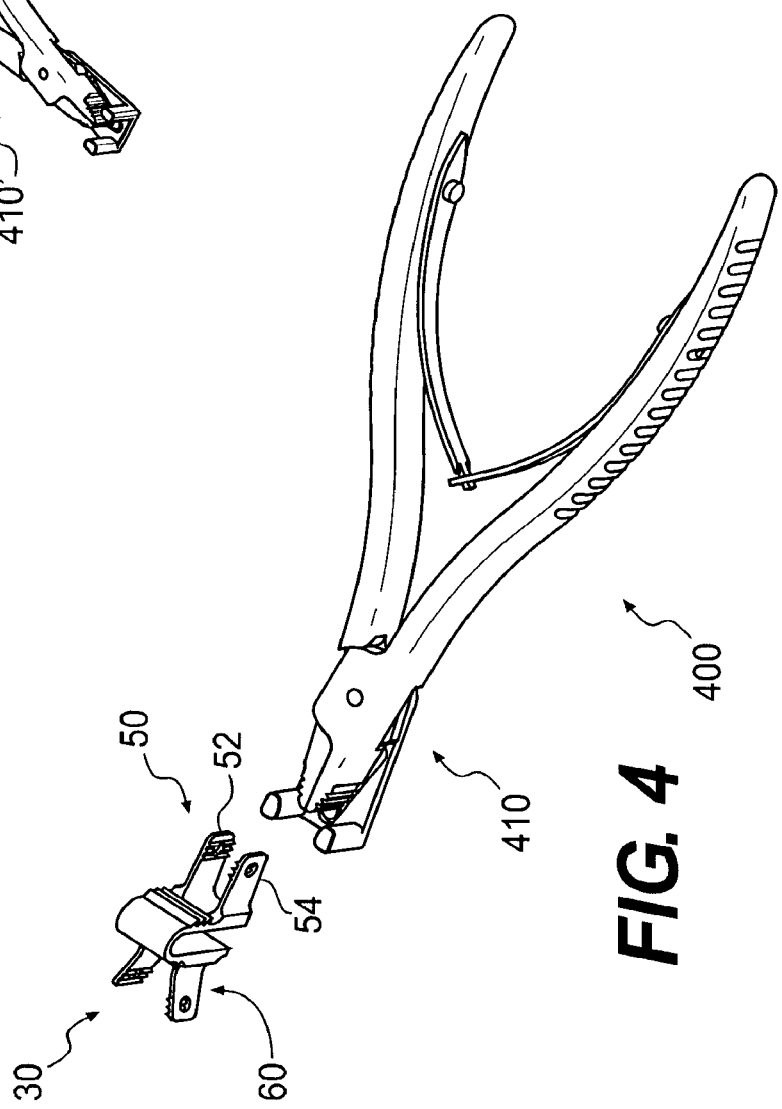

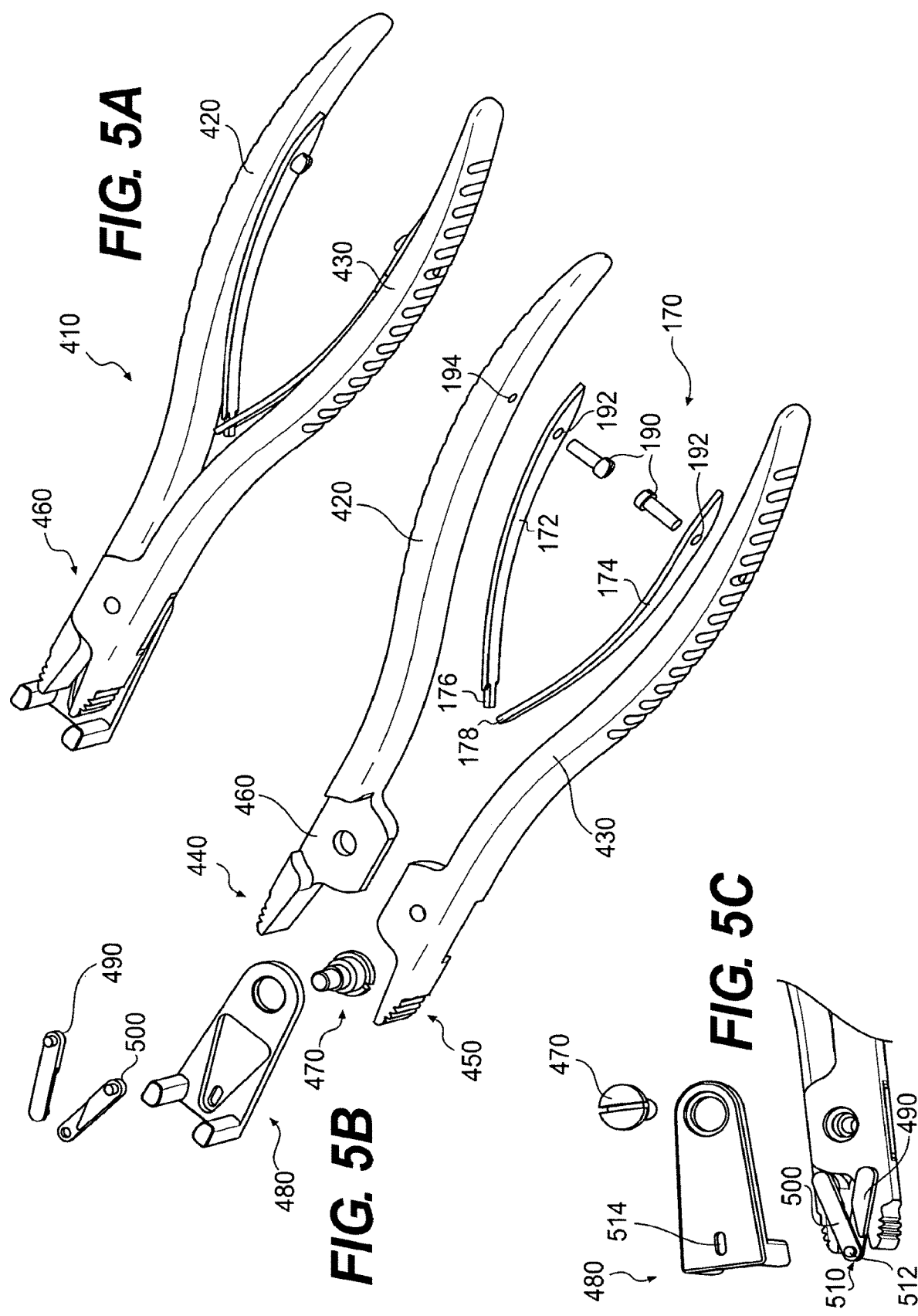

INSTRUMENT SYSTEM FOR USE WITH AN INTERSPINOUS IMPLANT

CROSS-REFERENCE TO RELATED APPLICATIONS

This application is a divisional of U.S. patent application Ser. No. 14/486,625, filed Sep. 15, 2014, now U.S. Pat. No. 10,070,898, which is a divisional of U.S. patent application Ser. No. 11/790,727, filed Apr. 27, 2007, now U.S. Pat. No. 8,834,482, which claims benefit of U.S. Provisional Application No. 60/796,256, filed Apr. 28, 2006, the entire contents of which are incorporated herein by reference.

FIELD OF THE INVENTION

The present invention relates to devices and methods for implanting and securing spinal implants. Specifically, the present invention pertains to surgical instruments and instrument systems for implanting interspinous devices.

BACKGROUND OF THE INVENTION

Diseases of the spine cause significant morbidity. These diseases include abnormalities of the vertebrae, the intervertebral discs, the facet joints, and connective tissue around the spine. Such abnormalities can be caused by a number of factors, such as mechanical injury, and can include degenerative disc disease, instability to the spine, vertebral misalignment, and abnormal motion between adjacent vertebrae. More severe disease may result in wear to the vertebral bony surfaces or cause nerve compression, and may ultimately produce severe pain. Further, these conditions are often chronic and progressive problems.

The treatments for spinal disorders may include long-term medical management or surgery. Medical management is generally directed at controlling the symptoms, such as pain, rather than correcting the underlying problems. For some patients this may require chronic use of pain medications, which may alter patient mental state or cause other negative side effects.

Another treatment option is surgery, which is often highly invasive and may significantly alter the existing spinal anatomy and function. For example, one surgical treatment for certain spinal conditions includes spinal fusion, whereby two or more vertebrae may be joined using bone grafts and/or synthetic implants. Fusion is irreversible and may significantly alter vertebral range-of-motion. Further, current surgical procedures are often only applicable to patients in a significantly progressed disease state.

Consequently, spinal surgeons have begun to develop more advanced surgical procedures and spinal stabilization and/or repair devices that are less invasive, may be reversible, and cause a less drastic alteration in the patient's normal anatomy and spinal function. These procedures may be used at an earlier stage of disease progression and, in some situations, may halt or reverse disease progression. For example, some spinal treatment systems include interspinous devices. Interspinous devices may be implanted between the spinous processes of two vertebrae or between the spinous process of the L5 vertebrae and the sacrum. These devices may provide various degrees of controlled movement of the spine, while supporting the adjacent vertebrae.

Some interspinous devices include an interspinous body portion that is anchored to adjacent spinous processes by wings extending from the body portion on opposite sides of the spinous process. Further, in some cases, the wings may be formed from a malleable material such as titanium. To facilitate implantation and secure attachment of the wings to the spinous processes, it may be desirable to bend or crimp the wings to control the distance between wings on opposite sides of a spinous process. However, bending or crimping the wings may be difficult using typical surgical instruments. Further, it may be desirable to bend or crimp opposing wings evenly to ensure appropriate attachment to the spinous process and to prevent undesirable distortion of the implant shape.

The present disclosure provides surgical instruments and instrument sets for use with interspinous devices. The surgical instruments may facilitate bending and/or crimping of interspinous devices to facilitate implantation and secure attachment of the devices to spinous processes.

SUMMARY OF THE INVENTION

One aspect of the present disclosure includes a surgical instrument. The instrument may include a first elongated section having a first surface region configured to contact an implantable device and a second elongated section having a second surface region configured to contact the implantable device. The instrument may further include a hinge region connecting the first elongated section to the second elongated section such that the first surface region of the first elongated section and second surface region of the second elongated section are mobile with respect to one another. Further, the instrument may include a guide member operatively connected to the first elongated section and second elongated section at the hinge region such that during movement of the first surface region of the first elongated section and second surface region of the second elongated section the guide member is maintained at a fixed symmetrical position with respect to the first surface region of the first elongated section and second surface region of the second elongated section.

A second aspect of the present disclosure includes a surgical instrument set. The instrument set may include a spinal implant and a surgical instrument. The implant may include a first implant body portion and at least two elongated wing members configured to engage opposite sides of a vertebral spinous process. The instrument may include a first elongated section having a surface region configured to contact an implantable device and a second elongated section having a second surface region configured to contact the implantable device. The instrument may further include a hinge region connecting the first elongated section to the second elongated section such that the first surface region of the first elongated section and second surface region of the second elongated section are mobile with respect to one another. Further, the instrument may include a guide member operatively connected to the first elongated section and second elongated section at the hinge region such that during movement of the first surface region of the first elongated section and second surface region of the second elongated section the guide member is maintained at a fixed symmetrical position with respect to the first surface region of the first elongated section and second surface region of the second elongated section.

A third aspect of the present disclosure includes a method of securing an implant adjacent a spinous process. The method may include selecting an implant having a first body portion and at least two elongated wing members configured to engage opposite sides of a vertebral spinous process. The method may further include positioning the first body portion adjacent a first spinous process and substantially evenly displacing each wing member in a first direction relative to a center point between the two elongated wing members to move the two elongated wing members toward one another to secure the elongated wing members on opposite sides of a spinous process.

A fourth aspect of the present disclosure includes a surgical instrument. The instrument may comprise a first surface configured to contact a portion of an implantable device and a second surface configured to contact a portion of an implantable device. The instrument further includes a first handle portion connecting the first surface and configured to translate a force to the first surface and a second handle portion connected to the second surface and configured to translate a force to the second surface. In addition, the device includes a guide member configured to center and hold the implantable device relative to the surgical instrument in a manner that permits the first and second surfaces to substantially evenly displace the first and second portions of the implant as the first and second surfaces contact the implantable device.

It is to be understood that both the foregoing general description and the following detailed description are exemplary and explanatory only, and are not restrictive of the invention, as claimed.

The accompanying drawings, which are incorporated in and constitute a part of this specification, illustrate several embodiments of the invention and together with the description, serve to explain the principles of the invention.

Additional objects and advantages of the invention will be set forth in part in the description that follows or may be learned by practice of the invention. The objects and advantages of the invention will be realized and attained by means of the elements and combinations particularly pointed out in the appended claims.

BRIEF DESCRIPTION OF THE DRAWINGS

FIG. 4 illustrates another portion of a surgical kit, including a surgical instrument and an implant, according to an exemplary disclosed embodiment.

FIG. 5D illustrates a perspective view of another surgical instrument, according to another exemplary disclosed embodiment.

FIG. 5A illustrates another perspective view of the surgical instrument of FIG. 4, according to an exemplary disclosed embodiment.

FIG. 5B illustrates an exploded view of the surgical instrument of FIG. 5A, according to an exemplary disclosed embodiment.

FIG. 5C illustrates an exploded view of an end region of the surgical instrument of FIG. 5A, according to an exemplary disclosed embodiment.

DESCRIPTION OF EXEMPLARY EMBODIMENTS

Reference will now be made in detail to the present exemplary embodiments of the invention, examples of which are illustrated in the accompanying drawings. Whenever possible, the same reference numbers will be used through out the drawings to refer to the same or like parts.

Implantable interspinous devices 30 can be used to treat a variety of surgical conditions, including, for example, degenerative disc disease and spinal stenosis. These devices 30 generally include an interspinous body portion 40 that is placed between the spinous processes of adjacent vertebrae, or the L5 spinous process and the sacrum. The devices 30 further include structures that allow the interspinous body to be secured between the spinous processes. For example, some devices can include a pair of wings 50, 60 that extend on opposite sides of a spinous process.

The interspinous body portion of an interspinous implantable device may be provided in a variety of different sizes to facilitate implantation into interspinous spaces (the space between two adjacent interspinous processes) of different sizes. However, the wing portions of such interspinous devices may need to be adjusted to allow implantation around a selected spinous process, and to provide sufficient compressive force to the spinous process to secure the implant in place.

To facilitate adjustment of the space between the wings and the resultant "fit" of the device relative to the spinous processes, surgical instruments to bend or expand the wings during insertion of the device into the interspinous space and to crimp or compress the wings after implantation of the device are provided. These surgical instruments may be sold separately or sold in a kit with one or more implants. One or both of the surgical instruments may be provided in the kit. The surgical instruments may be used in separate procedures or together in the same procedure. For example, it may be necessary only to crimp or compress the wings during the surgical procedure and unnecessary to expand or spread the wings prior to insertion. Alternatively, it may be necessary to spread or expand the wings prior to insertion and unnecessary to subsequently compress or crimp the wings after insertion of the interspinous implant.

Figure 1:
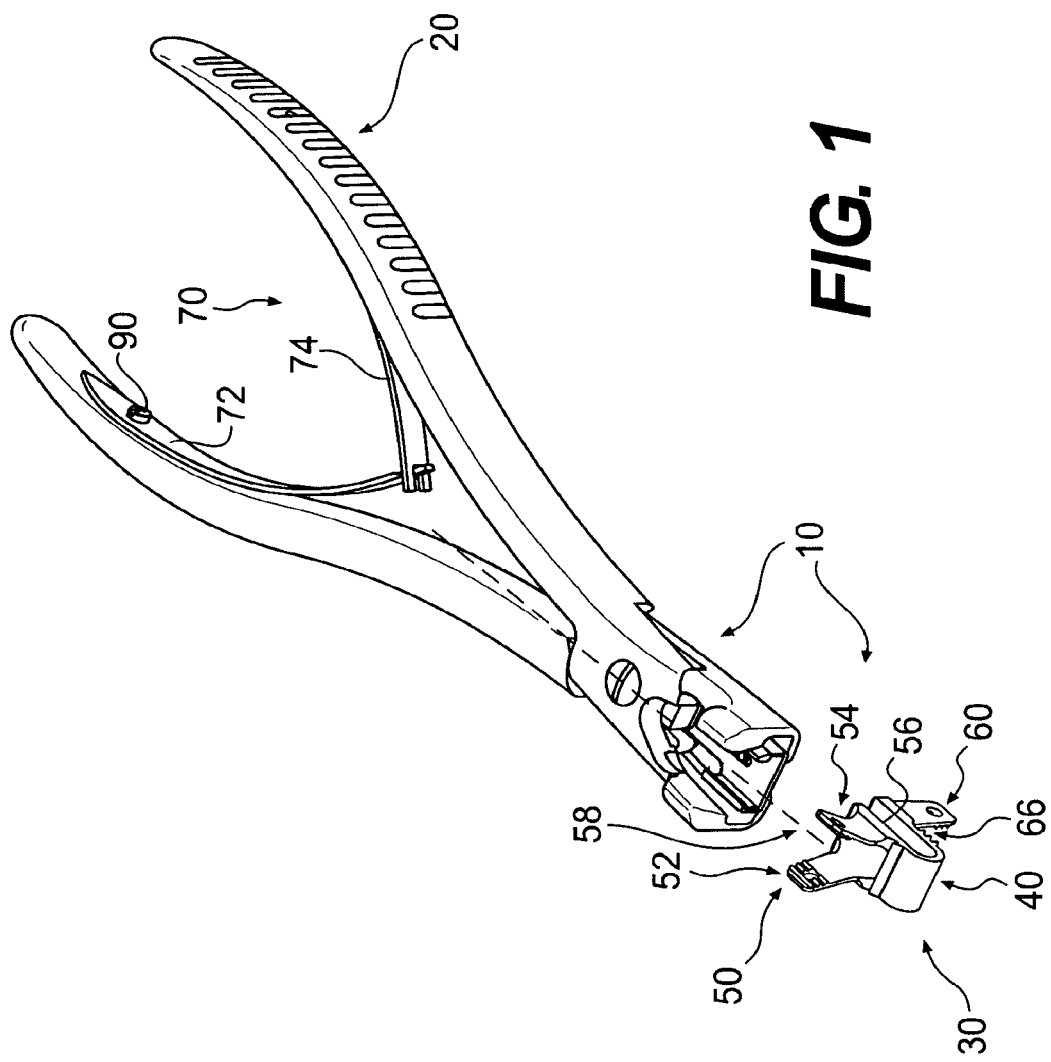
FIG. 1 illustrates a portion of a surgical kit, including a surgical instrument and an implant, according to an exemplary disclosed embodiment.

FIG. 1 illustrates a portion of a surgical kit or system 10, including a surgical instrument 20 and an implantable device 30, according to an exemplary disclosed embodiment. As shown, implantable device 30 comprises an interspinous implant. Implantable device 30 may include a U-shaped body portion 40 configured to be positioned below a spinous process (not shown). Implantable device 30 may further include at least one pair of wings 50, including a first wing 52 and second wing 54. Pair of wings 50 may extend from an upper surface 56 of body portion 40 and may be configured to engage a spinous process when implanted. Further, in some embodiments, implantable device 30 may include a second pair of wings 60 that may extend from a lower surface 66 of body portion 40 and may be configured to engage a second spinous process (not shown). Exemplary implants suitable for use with the present surgical instrument 20 and included with the instrument set 10 are described in detail in U.S. Pat. No. 5,645,599 to Jacques Samani, which is titled, "Interspinal Vertebral Implant," and U.S. Pat. No. 7,922,750 filed Nov. 29, 2007 and entitled "Interspinous Vertebral Stabilization System" both of which are hereby incorporated by reference in their entirety.

In some embodiments, the surgical instruments of the present disclosure will facilitate symmetric adjustment of the wings 52, 54 of implantable interspinous devices 30. For example, to ensure appropriate placement and securement of a device 30, it may be desirable to bend the wings 52, 54 symmetrically to center the spinous process between the wings and/or provide an appropriate compressive force to the spinous process. However, due to variations in design tolerances and production, the thicknesses of the wings 52, 54 may vary slightly from one another, which could affect the ease with which they bend or the amount of bending achieved, and thus produce asymmetric bending on opposing wings. The surgical instruments of the present disclosure can facilitate symmetric. bending by ensuring symmetric displacement of the wings to compress the wings 52, 54 onto a spinous process or to expand the wings 52, 54 before implantation. This symmetric displacement of the wings can be accomplished even with variations in wing thickness or material properties.

Surgical instrument 20 may be used to facilitate secure attachment of implantable device 30 to bone. As described below, instrument 20 may be used to bend or compress the pair of wings 50 or the pair of wings 60, thereby crimping the wings of a pair of wings 50, 60 to a spinous process therebetween. Further, although FIG. 1 illustrates an exemplary embodiment of implantable device 30 that may be included in surgical system 10, it is understood that any suitable implantable device may be selected wherein implantable device 30 includes at least one pair of wings 50, 60 that may be compressed by surgical instrument 20 and configured to secure implantable device 30 to at least one spinous process. Additionally, surgical instrument 20 may be adapted to be used to crimp extending portions of implants intended to be used in areas other than the spine. For example, some interspinous implants may be adapted for placement between the L5 spinous process and the sacrum. Exemplary interspinous implants that may be used for treatment of the lumbosacral region are described in detail in U.S. Pat. No. 8,470,000, to Frank Trautwein et al., which is titled, "Interspinous Vertebral and Lumbosacral Stabilization Devices and Methods of Use," and which is hereby incorporated by reference in its entirety.

In some embodiments, the surgical instruments of the present disclosure will facilitate symmetric adjustment of the wings 52, 54 of implantable interspinous devices 30. For example, to ensure appropriate placement and securement of a device 30, it may be desirable to bend the wings 52, 54 symmetrically to center the spinous process between the wings and/or provide an appropriate compressive force to the spinous process. However, due to small variations in design tolerances and production, the wings 52, 54 may have small variations in thickness which could affect the easy with which they bend, and produce asymmetric bending on opposing wings. The surgical instruments of the present disclosure can facilitate symmetric bending by ensuring symmetric displacement of the wings to compress the wings 52, 54 onto a spinous process or to expand the wings 52, 54 before implantation. This symmetric displacement of the wings can be accomplished even with variations in wing thickness or material properties.

Figure 2A:
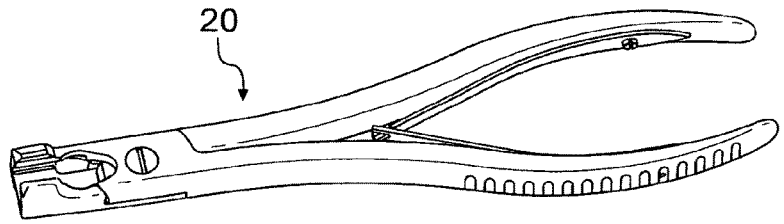
FIG. 2A illustrates a perspective view of the surgical instrument of the surgical kit of FIG. 1, according to an exemplary disclosed embodiment.
Figure 2B:
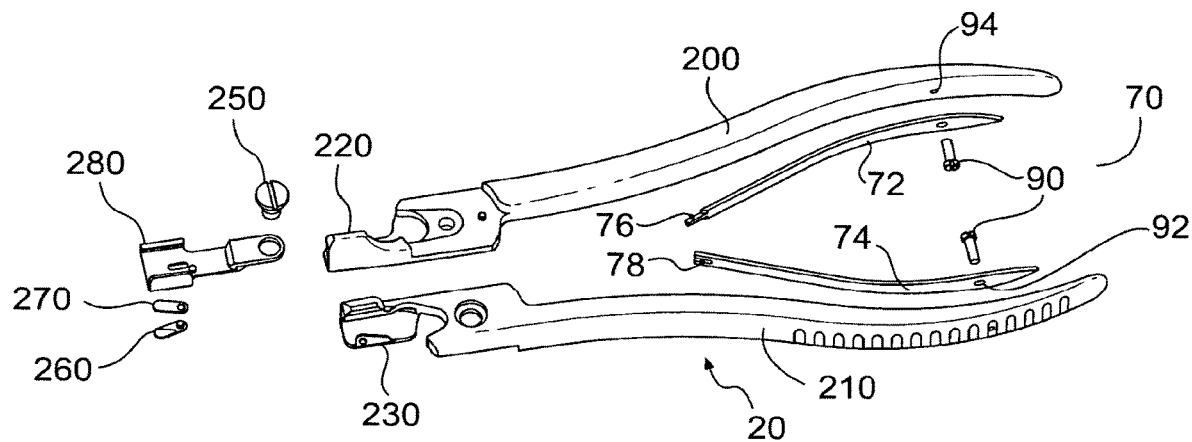
FIG. 2B illustrates an exploded view of the surgical instrument of FIG. 2A without a guide member, according to an exemplary disclosed embodiment.
Figure 2C:
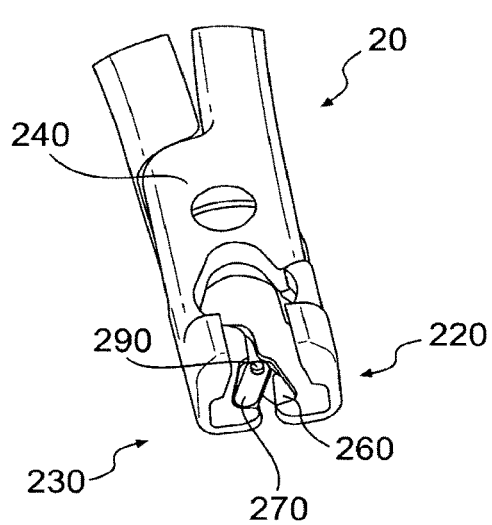
FIG. 2C illustrates a perspective view of an end region of the surgical instrument of FIG. 2A without a guide member, according to an exemplary disclosed embodiment.
Figure 2D:
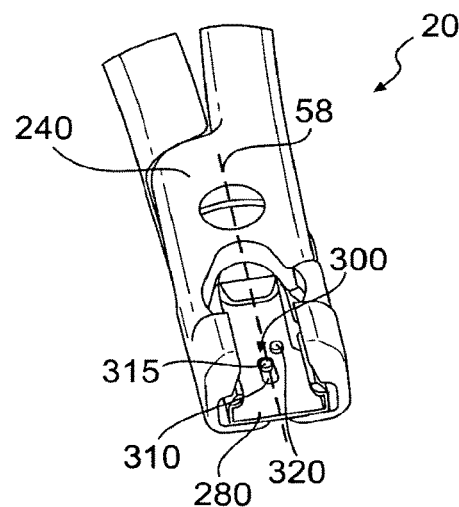
FIG. 2D illustrates a perspective view of an end region of the surgical instrument of FIG. 2A with a guide member, according to an exemplary disclosed embodiment.

FIG. 2A illustrates a perspective view of surgical instrument 20 of FIG. 1, according to an exemplary disclosed embodiment, and FIG. 28 illustrates an exploded view of surgical instrument 20 of FIG. 2A. As shown in FIGS. 2A and 28, instrument 20 includes a first handle portion 200 and a second handle portion 210. First handle portion 200 may be connected with a first elongated section 220, and second handle portion 210 may be connected with a second elongated section 230. First and second handle portions 200, 210, may be integrally formed with first and second elongated sections 220, 230, respectively. Alternatively, the elements may be separately formed and then connected. Further, first handle portion 200 and second handle portion 210 may be operatively connected to one another at a hinge region 240, as indicated in FIGS. 2C and 2D. Hinge region 240 may include a hinge connector 250, as shown in FIG. 2B. Hinge connector 250 may include any suitable connector type, such as a screw, a bolt, a pin, or other suitable connector.

A leaf spring mechanism 70 may also be provided between first handle portion 200 and second handle portion 210 to provide a biased, resistance force between first and second handle portions 200, 210. Leaf spring mechanism 70 may comprise two leaf springs 72, 74. One of the leaf springs 72 may terminate at a male portion 76, while the other leaf spring 74 may terminate at a female portion 78, as shown. Leaf springs 72, 74 may rest against one another in a freely movable, hinged configuration. This hinged configuration enables leaf springs 72, 74 to freely pivot with respect to one another. Each of leaf springs 72, 74 may be attached to a respective handle portion 200, 210 with a fastener 90. As shown in detail in FIG. 2B, leaf springs 72, 74 may attach to first and second handle portions 200, 210, respectively, by securing fasteners 90 through holes 92 on leaf springs 72, 74, and into holes 94 of first and second handle portions 200, 210. Fastener 90 may comprise any suitable connector such as, for example, a screw, a bolt, or a pin, as is commonly used in the art.

A surgeon may grasp surgical instrument 20 by first handle portion 200 and second handle portion 210, and by increasing or decreasing the distance between first handle portion 200 and second handle portion 210, may correspondingly increase or decrease the distance between first elongated section 220 and second elongated section 230. In some embodiments, as the distance between first handle portion 200 and second handle portion 210 is increased, the distance between first elongated section 220 and second elongated section 230 will increase. Conversely, as the distance between first handle portion 200 and second handle portion 210 is decreased, the distance between first elongated section 220 and second elongated section 230 will decrease.

Hinge region 240 may include at least two connector pieces 260, 270 and a guide member 280. FIG. 2C illustrates a perspective view of an end region of surgical instrument 20 of FIG. 2A without a guide member. As shown, first connector piece 260 may form a rotatably mobile connection with first elongated section 220, and second connector piece 270 may form a rotatably mobile connection with second elongated section 230. Connector pieces 260, 270 may further form a common rotatably mobile connection 290 with one another. Further, common connection 290 may form a second common connection 300 with guide member 280, as shown in FIG. 2D. Connector pieces 260, 270 may secure guide member 280 in a fixed position relative to first elongated section 220 and second elongated section 230 during movement of first elongated section 220 and second elongated section 230 about hinge region 240.

Guide member 280 and connector pieces 260, 270 may facilitate symmetric displacement of wings 52, 54. For example, as noted previously, due to design tolerances and production variables, the thicknesses and material properties of wings 52, 54 may vary slightly. Therefore, if equal bending forces are applied to each wing 52, 54 the displacement or degree of bending achieved for each wing 52, 54 may vary, thereby producing asymmetric engagement with a spinous process. The guide member 280 and connector pieces 260, 270 provide symmetric displacement of wings 52, 54 even when the dimensions and/or material properties of wings 52, 54 are different.

In some embodiments, the connection between guide member 280 and connector pieces 260, 270 may include a slidable connection. For example, as shown in FIG. 2D, guide member 280 may include a groove 310 in which a protrusion 315 from one connector piece 260, 270 rests. In some embodiments, groove 310 may include an elongated groove aligned with a central longitudinal axis 58 of surgical instrument 20, as shown in FIG. 2D.

Figure 2E:
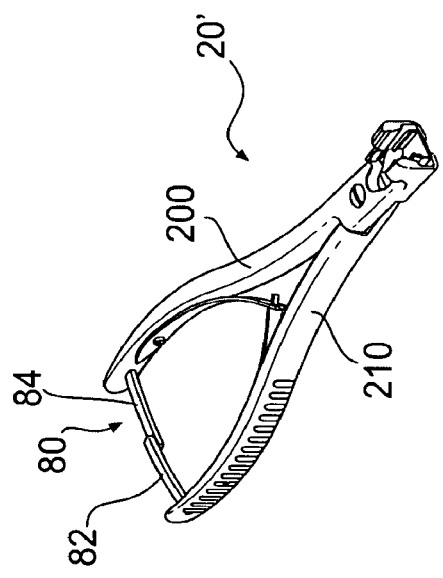
FIG. 2E illustrates a perspective view of an alternative configuration of the surgical instrument of FIG. 2A, according to another exemplary disclosed embodiment.
Figure 2F:
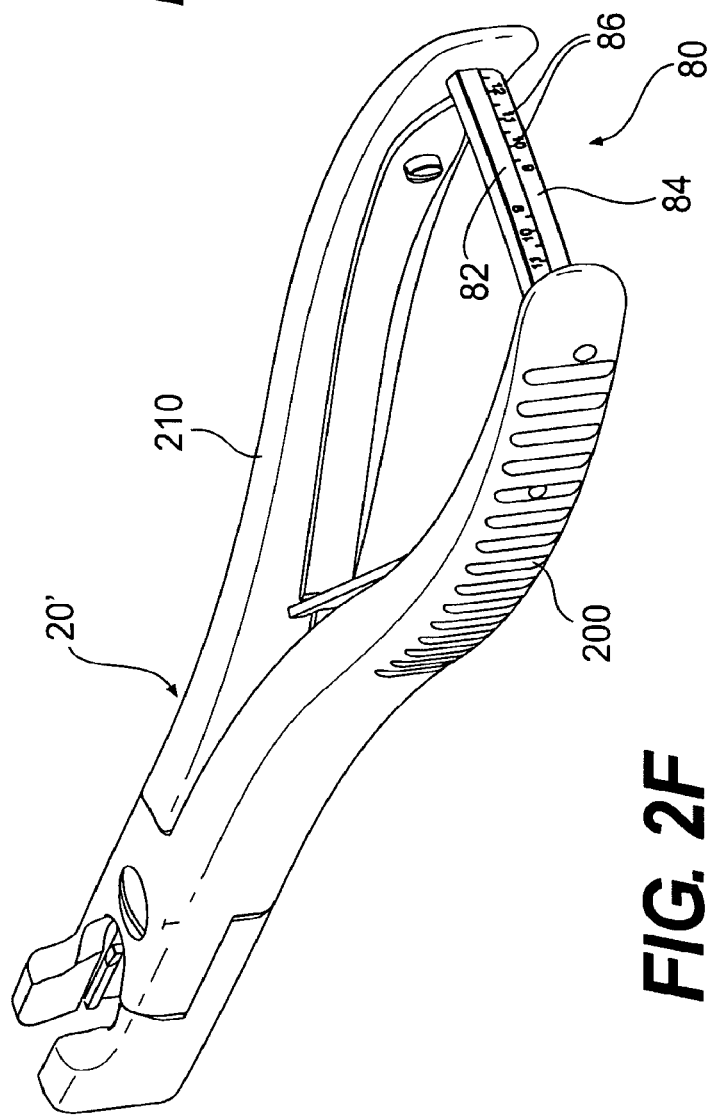
FIG. 2F illustrates another perspective view of the surgical instrument of FIG. 2E.

FIG. 2E illustrates a perspective view of a surgical instrument 20', according to another exemplary disclosed embodiment. Surgical instrument 20' is identical to surgical instrument 20, but with an additional visual gauge element 80. As shown in greater detail in FIG. 2F, the gauge element 80 comprises two arms 82, 84, each arm being attached to a handle region 200, 210, respectively, of surgical instrument 20'. The free ends of arms 82, 84 are configured to slide against one another when the surgical instrument 20' is engaged. Marks 86 on arms 82, 84 are aligned as the surgical instrument 20' is compressed or squeezed together, thereby indicating to the user the distance between the pair of wings 50, 60. Marks 86 may include numerals, scores, color-coded bars, or other visual indicators which are intended to line up on arms 82, 84. Thus, gauge element 80 helps to make surgical instrument 20' function much like a caliper. In this manner, surgical instrument 20' may also serve as a measuring device, allowing the user to measure the distance between the pair of wings 50, 60 prior to or after implantation.

Figure 3A:
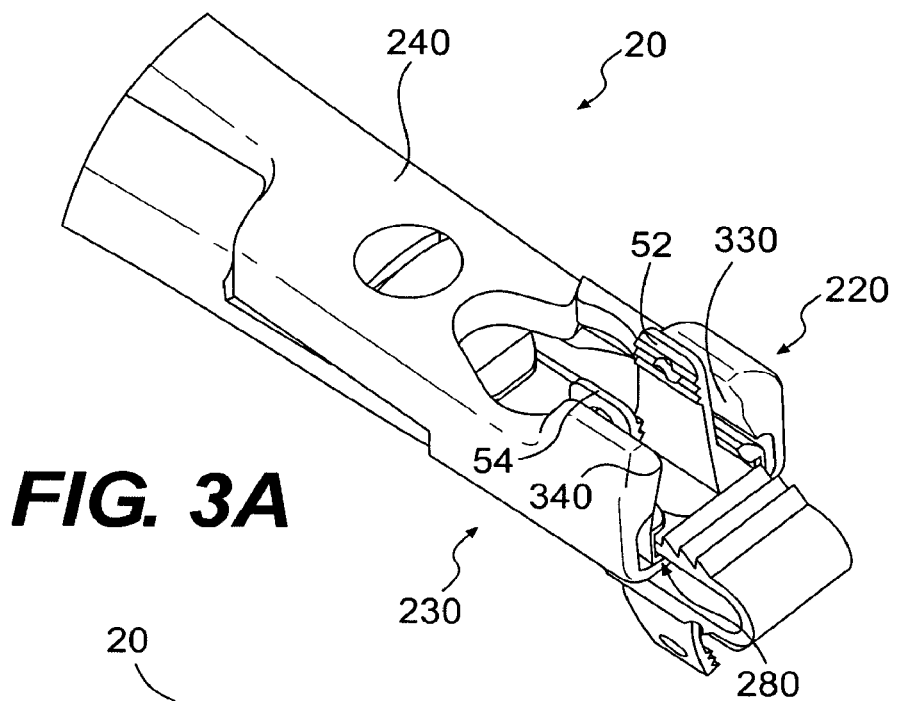
FIG. 3A illustrates a perspective view of the surgical instrument of FIG. 2A engaging an interspinous implant.

As noted previously, surgical instrument 20 may be used as crimping pliers to compress or bend pair of wings 50, 60 of implantable device 30. FIG. 3A illustrates a perspective view of the surgical instrument 20 of FIG. 2A engaging interspinous implantable device 30. First elongated section 220 may include a first surface 330 configured to engage a first wing 52 of pair of wings 50 and to exert a compressive force on first wing 52. Second elongated section 230 may include a second surface 340 configured to engage a second wing 54 of pair of wings 50 and to exert a compressive force on second wing 54. Further, guide member 280, being operably connected to first elongated section 220 and second elongated section 230 by connector pieces 260, 270, may facilitate the production of a symmetric displacement or bending of wings 52, 50 of pair of wings 50, and/or application of approximately symmetric compressive forces on first wing 52 and second wing 54. As shown, guide member 280 may be configured to securely and properly hold implantable device 30, thereby ensuring the appropriate engagement and alignment of first and second surfaces 330, 340 with pair of wings 50 to allow evenly applied bending or crimping force, and produce symmetric displacement or bending of pair of wings 50.

Figure 3B:
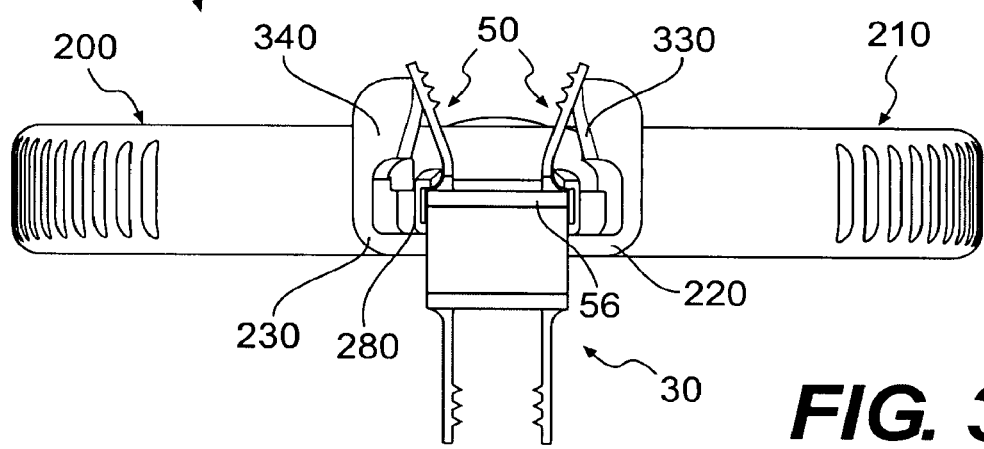
FIG. 3B illustrates an end view of the surgical instrument of FIG. 2A engaging an interspinous implant before compression of the implant's wings.
Figure 3C:
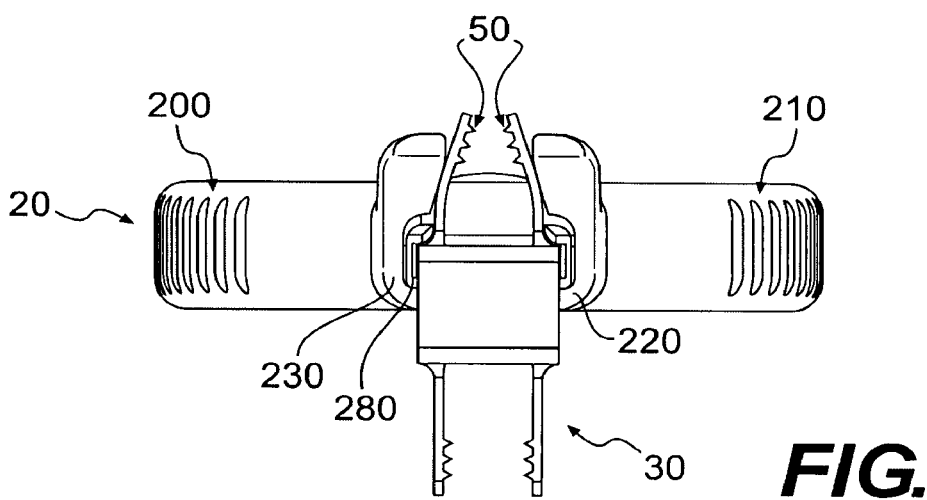
FIG. 3C illustrates an end view of the surgical instrument of FIG. 2A engaging an interspinous implant after compression of the implant's wings.

FIG. 3B illustrates an end view of surgical instrument 20 of FIG. 2A engaging interspinous implantable device 30 before compression of implant wings 50. As noted previously, guide member 280 may be configured to engage top a surface 56 of device 30. Further, first elongated section 220 and second elongated section 230 may be positioned on opposite sides of implantable device 30 and may engage outer surfaces of wings 52, 54. As shown, first handle portion 200 and second handle portion 210 are in an open position, and a surgeon may compress first handle 200 and second handle 210 together to move first elongated section 220 and second elongated section 230 toward one another and thereby apply a compressive force to the wings 52, 54 sufficient to bend wings 52, 54 inward, as shown in FIG. 3C, to engage a spinous process (not shown) located therebetween.

It is also contemplated that the surgeon may elect to use the surgical instrument 20 to pre-bend the implantable device 30 prior to insertion, such as for example, where the spinous process is relatively thin and the surgeon may decide that a pre-shaped or preloaded implantable device (i.e., one where the wings 52, 54 of a pair of wings 50 are crimped together to form a narrower gap therebetween) would enable a better fit. Alternatively, the surgeon may elect to use surgical instrument 20 to pre-bend implantable device 30 prior to insertion such that the distance or gap between wings 52, 54 is slightly smaller than the width of the spinous process to be placed therebetween. This latter scenario may be desirable for a surgeon when taking into account the degree of flexibility or elasticity of wings 50, 60, which would enable wings 50, 60 to act as a clip on a spinous process.

Figure 3D:
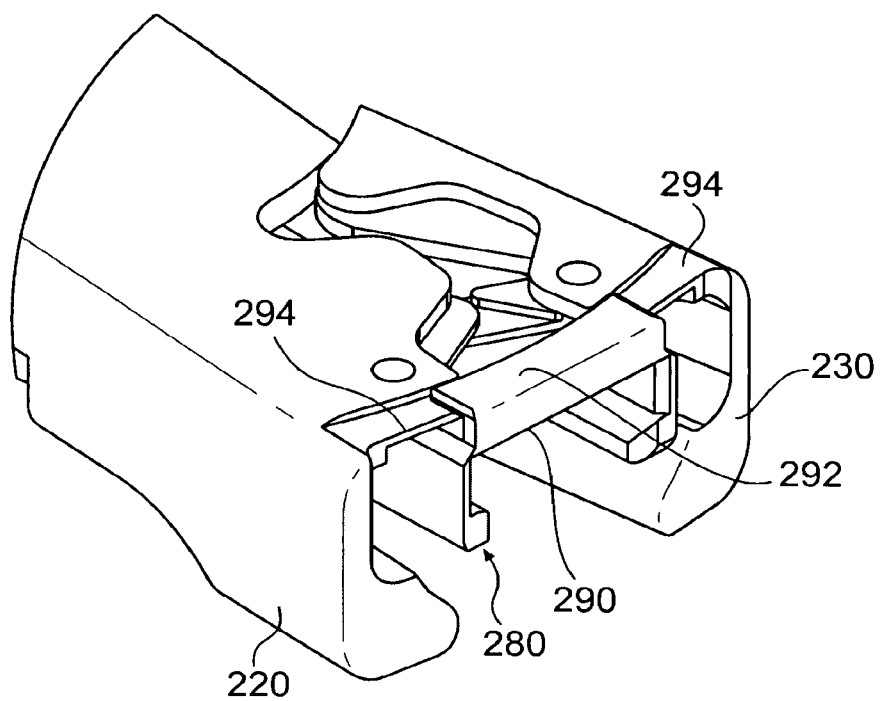
FIG. 3D illustrates a perspective view of the underside of the end region of the surgical instrument of FIG. 3A, according to an exemplary embodiment.

FIG. 3D illustrates a perspective end view of the underside of the surgical instrument of FIG. 3A, according to an exemplary embodiment. As shown, guide member 280 can include a distal extension 290. Distal extension 290 can provide a relatively thicker material region that will provide additional rigidity to guide member 280, thereby preventing bending of guide member 280 during use. In some embodiments, distal extension 290 can further include a hook section 292 configured to overlap end region 294 of first elongated section 220 and second elongated section 230, thereby further preventing bending of guide member 280.

As noted previously, guide member 280 may be maintained at a fixed symmetric position with respect to first elongated section 220 and second elongated section 230. As guide member 280 may engage implantable device 30 before compression, the fixed relative position of guide member 280 may facilitate equal distribution of compressive forces on wings 52, 54. This configuration may assist a surgeon in securely attaching implantable device 30 to a spinous process by securing wing 52 and wing 54 in approximately symmetric alignment with the spinous process.

In some embodiments, surgical instrument 20 can include additional mechanisms to aid a physician in properly positioning instrument 20 on implant 30. For example, referring again to FIG. 2D, instrument 20 can include a blocking protrusion 320 positioned on guide member 280. Blocking protrusion 320 can be positioned on an upper surface of guide member 280 such that it will contact a portion of implant 30 engaged by guide member 280 and prevent implant 30 from moving too far into guide member 280. Further, it will be understood that the position and size of blocking protrusion 320 can be selected based on the size and configuration of a selected implant 30 and/or instrument 20.

FIG. 4 illustrates a portion of a kit or surgical set 400, including a surgical instrument 410 and implantable device 30, according to an exemplary disclosed embodiment. As shown, implantable device 30 may comprise an interspinous implant similar to that described above with reference to FIG. 1. As noted previously, implantable device 30 may include at least one pair of wings 50, which may be configured to engage a spinous process (not shown). During an implantation procedure, a surgeon can determine that the distance between first wing 52 and second wing 54 is insufficient to allow the implant to be properly implanted, i.e., the spinous process is too large to fit between wings 52, 54. Therefore, it may be desirable to spread wings 52, 54 apart, thereby increasing the distance between first wing 52 and second wing 54. Surgical instrument 410 may be used to increase the distance between wings 50 to facilitate implantation. Further, instrument 410 may be configured to provide equal bending forces to both wings 52, 54 of pair of wings 50 to bend wings 52 and wing 54 substantially symmetrically.

FIG. 5A illustrates a perspective view of surgical instrument 410 of FIG. 4, according to an exemplary disclosed embodiment, and FIG. 5B illustrates an exploded view of the surgical instrument of FIG. 5A. As shown, instrument 410 includes a first handle portion 420 and a second handle portion 430. First handle portion 420 may be connected to a first elongated section 440, and second handle portion 430 may be connected to a second elongated section 450. First handle portion 420 may be integrally formed with first elongated section 440, and second handle portion 430 may be integrally formed with second elongated section 450. Alternatively, the pieces may be separately formed and then joined. Further, first handle portion 420 and second handle portion 430 may be joined at a hinge region 460. Hinge region 460 may form a rotatable connection between first handle portion 420 and second handle portion 430. As shown, hinge region 460 may include a hinge connector 470, such as, for example, a screw, a pin, a bolt, or another type of suitable connector.

Similar to surgical instrument 20 previously described, a leaf spring mechanism 170 may also be provided between the first handle portion 420 and the second handle portion 430 to provide a biased resistance-force between handle portions 420, 430. Leaf spring mechanism 170 may comprise two leaf springs 172, 174. One leaf spring 172 may terminate into a male portion 176, while another leaf spring 174 may terminate into a female portion 178, as shown. Leaf springs 172, 174 may rest against one another in a mobile, hinged configuration. This hinged configuration enables leaf springs 172, 174 to pivot with respect to one another. Each of leaf springs 172, 174 may be attached to handle portions 420, 430 with a fastener 190. As shown in detail in FIG. 5B, leaf springs 172, 174 may attach to first and second handle portions 420, 430, respectively, by securing fasteners 190 through holes 192 on leaf springs 172, 174, and into holes 194 of the first and second handle regions 420, 430. Fasteners 190 may comprise any suitable connector such as, for example, a screw, a bolt, or a pin, as is commonly used in the art.

A surgeon may grasp first handle portion 420 and second handle portion 430, and by increasing or decreasing the distance between first handle portion 420 and second handle portion 430, may increase or decrease the distance between first elongated section 440 and second elongated section 450. In one embodiment, as the distance between first handle portion 420 and second handle portion 430 is increased, the distance between first elongated section 440 and second elongated section 450 will decrease. Conversely, as the distance between first handle portion 420 and second handle portion 430 is decreased, the distance between first elongated section 440 and second elongated section 450 will increase.

FIG. 5C illustrates an exploded view of an end region of the surgical instrument 410 of FIG. 5A, according to an exemplary disclosed embodiment. As shown, instrument 410 may further include a guide member 480 and at least two connector pieces 490, 500. First connector piece 490 may form a rotatably mobile connection with first elongated section 440, and second connector piece 500 may form a rotatably mobile connection with second elongated section 450. Connector pieces 490, 500 may further form a common rotatably mobile connection 510 with one another. Further, connection 510 may form a common connection with guide member 480. In some embodiments, at least one connector piece may include a protrusion 512 configured to engage an elongated groove 514 in guide member 480 to form a slidable connection between connector pieces 490, 500 and guide member 480. Connector pieces 490, 500 may be rotatably joined at protrusion 512 and may secure guide member 480 in a fixed symmetric position with respect to first elongated section 440 and second elongated section 450 during movement of first elongated section 440 and second elongated section 450 about hinge region 460.

Similar to guide member 280 and connector pieces 260, 270, guide member 480 and connector pieces 490, 500 may facilitate symmetric displacement of wings 52, 54. For example, as noted previously, due to design tolerances and production variables, the thicknesses and material properties of wings 52, 54 may vary slightly. Therefore, if equal bending forces are applied to each wing 52, 54 the displacement or degree of bending achieved for each wing 52, 54 may vary, thereby producing an asymmetric implant shape and possibly producing improper engagement with a spinous process when 52, 54 and bend towards one another after implantation. The guide member 480 and connector pieces 490, 500 provide symmetric displacement of wings 52, 54 even when the dimensions and/or material properties of wings 52, 54 are different.

FIG. 5D illustrates a perspective view of a surgical instrument 410', according to another exemplary disclosed embodiment. Surgical instrument 410' is identical to surgical instrument 410, but with an additional visual gauge element 180 similar to the one described with surgical instrument 20'.

The gauge element 180 comprises two arms 182, 184, each arm being attached to a handle region 420, 430, respectively, of the surgical instrument 410'. The free ends of the arms are configured to slide against one another when the surgical instrument 410' is engaged. Visual indicators or marks (not shown) on arms 182, 184 are aligned as the surgical instrument 410' is compressed or squeezed together, thereby indicating to the user the distance between implant wings 52, 64 as they are spread apart.

Figure 6A:
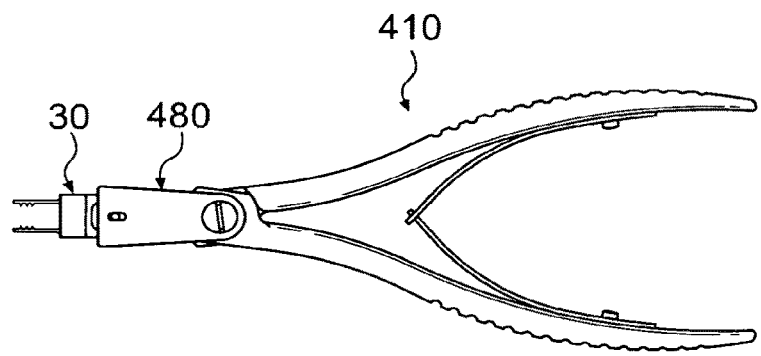
FIG. 6A illustrates a top view of the surgical instrument of FIG. 5A engaging an interspinous implant.
Figure 6B:
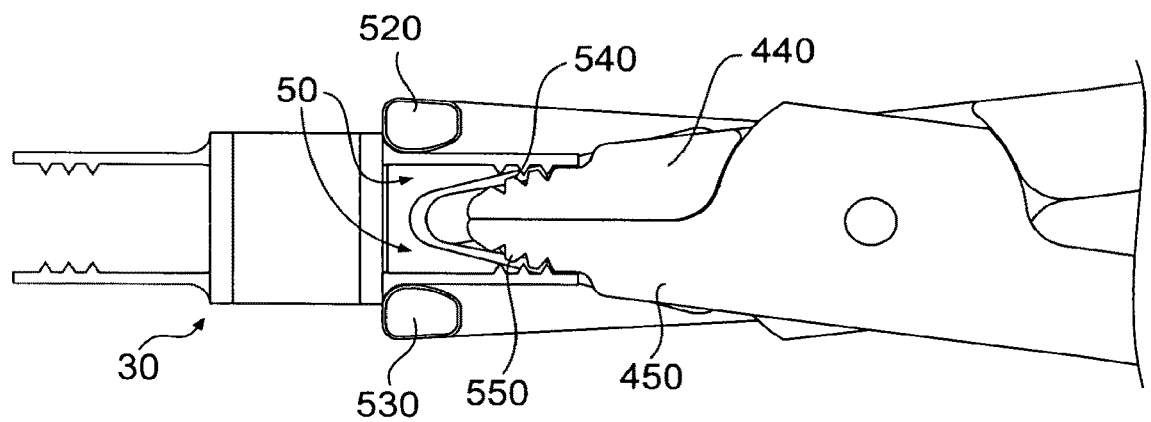
FIG. 6B illustrates an enlarged top view of a front end of the surgical instrument of FIG. 6A engaging an interspinous implant before expansion of the implant's wings.
Figure 6C:
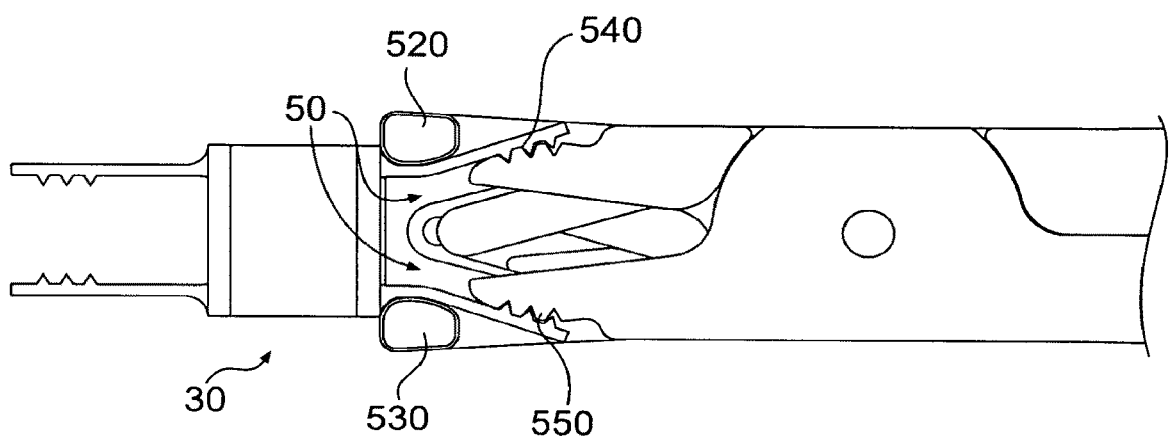
FIG. 6C illustrates an enlarged view of the surgical instrument of FIG. 6A engaging an interspinous implant after expansion of the implant's wings.

FIG. 6A illustrates a perspective view of surgical instrument 410 of FIG. 4 engaging an interspinous implant. As shown, guide member 480 is placed around pair of wings 50 of implantable device 30. FIG. 6B illustrates an enlarged top view of surgical instrument 410 of FIG. 6A engaging interspinous implantable device 30 before expansion of implant wings 50. As shown, guide member 480 includes two distal protrusions 520, 530 positioned adjacent to outer surfaces of wings 50. Distal protrusions 520, 530 may serve as guide ramps or bumpers, providing a support surface against which pair of wings 50 may be bent outward. Further, first elongated section 440 may include a surface 540, and second elongated section 450 may include a second surface 550. As a surgeon compresses handle portions 420, 430 together, first surface 540 and second surface 550 may move outwardly and exert an expanding force on wings 50, thereby spreading wings 50 apart, as shown in FIG. 6C. Thus, surgical instrument 410 may be used as spreading pliers to evenly expand the distance between pair of wings 50, 60 of implantable device 30 in order to accommodate an oversized interspinous process therebetween. In some embodiments, distal protrusions 520, 530 will be positioned equidistant from a long axis of instrument 410, thereby allowing wings 52, 54 to be evenly bent outward by applying force against wings 52, 54 and protrusions 520, 530.

It is contemplated that a surgical set or kit set 10 of the present invention may include one or more of surgical instruments 20, 410 and may include one or more of implantable devices 30. The surgical set or kit may further include a sizing implant for sizing an interspinous space that will receive an implant. Alternatively, it is possible to provide an instrument set without an implantable device and/or sizing implement. The surgical instruments 20, 410 may be configured specifically to be used with the implantable device 30 provided with the surgical set or kit. The surgical instruments 20, 410 can be calibrated to either bend together or spread apart a pair of wings 50, 60 within a predetermined range of angles and forces, so as not to overextend the wings 50, 60 and cause damage, weakening, or breakage.

To implant device 30, a surgeon will first expose the interspinous space to be treated using an incision near the selected vertebral levels. Next, the surgeon will partially or completely remove the posterior spinal ligaments at the selected vertebral level. Then, to make space for an implantable device 30, the surgeon will remove part or all of the interspinous ligament.

Figure 7A:
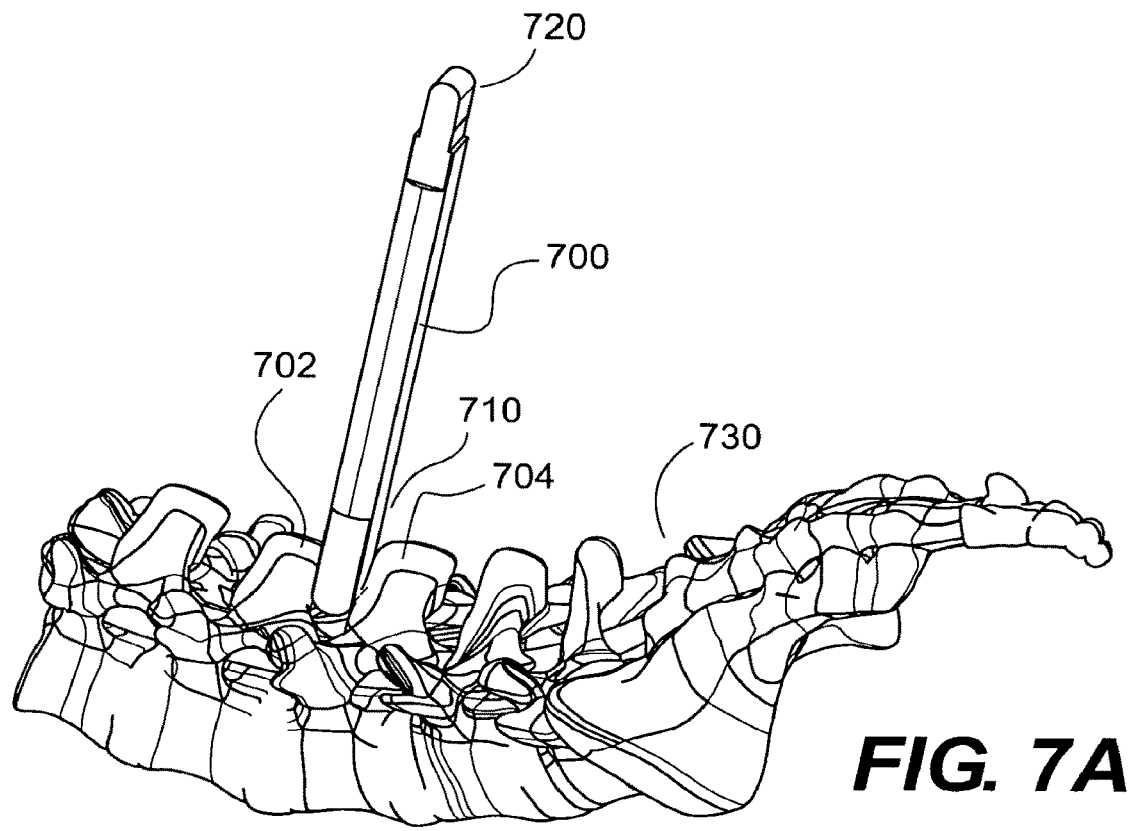
FIG. 7A illustrates a portion of a surgical kit, including a sizing and insertion implement, according to an exemplary disclosed embodiment.

Prior to implantation of implantable device 30, the surgeon may size and/or shape the selected interspinous space. FIG. 7A illustrates a portion of a surgical kit, including a sizing and insertion implement 700, according to an exemplary disclosed embodiment. As shown, implement 700 includes a first sizing end 710 that can be inserted between two spinous processes 702, 704. Sizing end 710 is configured to have a size and shape approximately matching the size and shape of an implantable device of a surgical kit, thereby allowing a surgeon to test the size of an implantable device before implantation. Further, as noted previously, the surgical kits of the present disclosure can include implants having a variety of different sizes, and accordingly, the kit can further include sizing implements corresponding to the size of each implant.

Figure 7B:
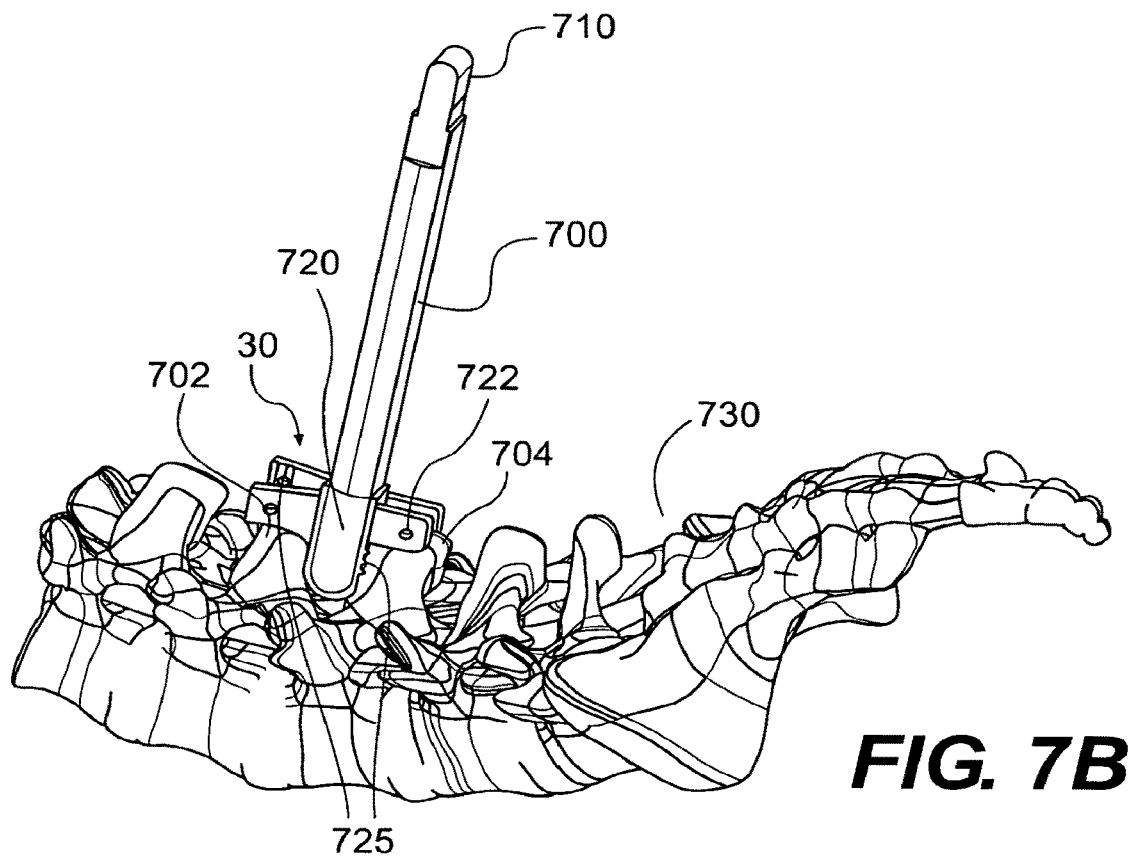
FIG. 7B illustrates the implement of FIG. 7A engaging an interspinous implant, according to an exemplary disclosed embodiment.

The surgical kits of the present disclosure can further include insertion implements. For example, in some embodiments, implement 700 can include a second implantation end 720. For example, FIG. 7B illustrates the implement of FIG. 7A engaging an interspinous implant 30, according to an exemplary disclosed embodiment. As shown, implantation end 720 is configured to engage a space between U-shaped body 40 of implant 30, thereby allowing a surgeon to manipulate device 30 and push device 30 into a selected anatomic space. Alternatively, surgical instrument 20, as described above, can be used to grasp an implant 30 to facilitate manipulation and insertion.

It should be noted that a number of variations to the implantation technique and selected implantable device are envisioned. For example, in some embodiments, the spinous processes may be cut or shaped prior to implantation of selected devices. Suitable devices for shaping spinous processes are described in detail in U.S. Pat. No. 9,011,441 to Rudolf Bertagnoli et al., which is titled, "Method and System for Performing Interspinous Space Preparation for Receiving an Implant," and which is hereby incorporated by reference in its entirety.

In addition, suitable implantable devices 30 can include surface projections 725, barbs, or other features on the device body or inner surfaces of the wing members. These surface projections 725 can further improve attachment of the device to spinous processes. In addition, in some embodiments, a surgeon may secure an implant to a spinous process by forming a hole transversely through the spinous process and placing a screw, rivet or other connection through the hole in the spinous process and through a hole 722 in at least one of the elongated wing members of an implantable device 30. Such a process is disclosed in U.S. Pat. No. 7,922,750, filed Nov. 29, 2007 and entitled "Interspinous Vertebral Stabilization System," which is hereby incorporated by reference in its entirety. Further, as noted previously, other suitable implantable devices can be selected, including devices used to treat various vertebral levels including vertebral levels adjacent the lumbosacral region 730.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A surgical instrument, comprising:
   a first elongated section having at least one first surface region configured to contact an interspinous device, the device having a pair of wings for receiving a spinous process and the at least one first surface region being configured to contact one of the pair of wings;
   a second elongated section having at least one second surface region configured to contact the other of the pair of wings of the interspinous device;
   a hinge region connecting the first elongated section to the second elongated section such that the first surface region of the first elongated section and second surface region of the second elongated section are mobile with respect to one another; and
   a guide member configured to hold the interspinous device and being operatively connected to the first elongated section and second elongated section at the hinge region such that, during movement of the first surface region of the first elongated section and second surface region of the second elongated section, the guide member is maintained at a fixed symmetrical position with respect to the first surface region of the first elongated section and second surface region of the second elongated section;

wherein, when the interspinous device is held by the guide member, movement of the first surface region and second surface region causes an expansion of a distance between the pair of wings.

2. The surgical instrument of claim 1, further including a first handle portion extending from the first elongated section and a second handle portion extending from the second elongated section.

3. The surgical instrument of claim 2, wherein the first handle portion and second handle portion are configured to move between a first, open position and a second, closed position.

4. The surgical instrument of claim 3, wherein movement of the first handle portion and second handle portion from the first, open position to the second, closed position causes the first surface region of the first elongated section and the second surface region of the second elongated section to move further apart.

5. A surgical kit, comprising:
at least one spinal implant, including:
an implant body; and
at least two elongated wing members configured to engage opposite sides of a vertebral spinous process;
at least one surgical instrument, including:
a first elongated section having at least one first surface region configured to contact one of the at least two elongated wing members of the at least one spinal implant;
a second elongated section having at least one second surface region configured to contact another of the at least two elongated wing members of the at least one spinal implant;
a hinge region connecting the first elongated section to the second elongated section such that the first surface region of the first elongated section and second surface region of the second elongated section are mobile with respect to one another; and
a guide member configured to hold the at least one spinal implant and being operatively connected to the first elongated section and second elongated section at the hinge region such that during movement of the first surface region of the first elongated section and the second surface region of the second elongated section the guide member is maintained at a fixed symmetrical position with respect to the first surface region of the first elongated section and the second surface region of the second elongated section;
wherein, when the at least one spinal implant is held by the guide member, movement of the first surface region and second surface region causes an expansion of a distance between the at least two elongated wing members.

6. The surgical kit of claim 5, wherein the surgical instrument further includes a first handle portion extending from the first elongated section and a second handle portion extending from the second elongated section.

7. The surgical kit of claim 6, wherein the first handle portion and second handle portion are configured to move between a first, open position and a second, closed position.

8. The surgical kit of claim 7, wherein movement of the first handle portion and second handle portion from the first, open position to the second, closed position causes the first surface region of the first elongated section and the second surface region of the second elongated section to move further apart.

9. The surgical kit of claim 5, wherein the at least one surgical instrument is a first surgical instrument and the kit further comprising a second surgical instrument.

10. The surgical kit of claim 9, wherein the second surgical instrument comprises:
a first elongated section having at least one first surface region configured to contact a portion of the at least one spinal implant;
a second elongated section having at least one second surface region configured to contact a portion of the at least one spinal implant;
a hinge region connecting the first elongated section to the second elongated section such that the first surface region of the first elongated section and second surface region of the second elongated section are mobile with respect to one another; and
a guide member operatively connected to the first elongated section and second elongated section at the hinge region such during movement of the first surface region of the first elongated section and second surface region of the second elongated section that the guide member is maintained at a fixed symmetrical position with respect to the first surface region of the first elongated section and second surface region of the second elongated section.

11. The surgical kit of claim 10, wherein the first and second surface regions of the first instrument are inner surfaces of the first and second elongated sections of the first instrument.

12. The surgical kit of claim 11, wherein the first and second surface regions of the second instrument are outer surfaces of the first and second elongated sections of the second instrument.

13. The surgical kit of claim 9, further comprising a plurality of spinal implants, each spinal implant including an implant body of a different size.

14. The surgical kit of claim 13, further comprising an implant insertion tool.

15. The surgical kit of claim 14, further comprising at least one sizing tool.

16. The surgical kit of claim 13, further comprising an implant insertion and sizing tool having a first end having a size and shape substantially equal to the size and shape of one of the plurality of implants and a second end configured to engage one of the plurality of implants to facilitate insertion of the one of the plurality of implants in an interspinous space.

17. A surgical instrument, comprising:
a first surface configured to contact a first portion of an implantable, interspinous device;
a second surface configured to contact a second portion of the implantable device, the first and second portions of the implantable, interspinous device defining a space for receiving a spinous process;
a first handle portion connected to the first surface and configured to translate a force to the first surface;
a second handle portion connected to the second surface and configured to translate a force to the second surface; and
a guide member configured to center and hold the implantable device relative to the surgical instrument in a manner that permits the first and second surfaces to substantially evenly displace the first and second portions of the implant as the first and second surfaces contact the implantable device;

wherein, when the implantable, interspinous device is held by the guide member, translation of the forces causes an expansion of a distance between the first and second portions of the implantable, interspinous device.

18. The surgical instrument of claim 17, wherein the first handle portion and second handle portion are configured to move between a first, open position and a second, closed position.

19. The surgical instrument of claim 18, wherein movement of the first handle portion and second handle portion from the first, open position to the second, closed position causes the first surface and the second surface to move further apart.

\* \* \* \* \*